United States Patent [19]

McGregor

[11] 4,371,466
[45] Feb. 1, 1983

[54] MAMMALIAN COLLAGENASE INHIBITORS

[75] Inventor: William H. McGregor, Malvern, Pa.

[73] Assignee: American Home Products Corporation, New York, N.Y.

[21] Appl. No.: 309,369

[22] Filed: Oct. 7, 1981

[51] Int. Cl.³ .................... C07C 103/52; A61K 37/00
[52] U.S. Cl. .................... 260/112.5 R; 424/177
[58] Field of Search ................. 424/177; 260/112.5 R

[56] References Cited

U.S. PATENT DOCUMENTS 4,235,885 11/1980 Sundoon et al. .................... 424/177
4,276,284 6/1981 Brown ................................ 424/177

FOREIGN PATENT DOCUMENTS 53028165 8/1976 Japan.

OTHER PUBLICATIONS

Harper, "Ann. Rev. Biochem." 1980, 49:1063–1078.
Ajinomoto KK, "Japanese Patent Abstract," 3028-165, 8-30-76.

Primary Examiner—Delbert R. Phillips
Assistant Examiner—F. T. Moezie
Attorney, Agent, or Firm—Richard K. Jackson

[57] ABSTRACT

The polypeptides $$X-R_1-R_2-[R_3]_n-NH_2$$

where
X is hydrogen, alkanoyl of 2 to 6 carbon atoms, cycloalkylcarbonyl of 6 to 8 carbon atoms or alkoxycarbonyl of 2 to 6 carbon atoms;
$R_1$ is Cys-, 3-mercapto-Val-, p-Glu-Cys-, p-Glu-3-mercapto-Val- or Pro-Gln-Gly-;
$R_2$ is Leu-, Ile- or Val-;
$R_3$ is Ala-, Ala-Gly- or Ala-Gly-Arg-; and
n is 0 or 1;

or a pharmaceutically acceptable salt thereof act as collagenase inhibitors useful in the treatment of diseases involving excessive tissue destruction by collagenase.

4 Claims, No Drawings

MAMMALIAN COLLAGENASE INHIBITORS

BACKGROUND OF THE INVENTION

Approximately thirty percent of the body protein of mammals is comprised of collagen, a long rod-like polypeptide containing three parallel chains of coiled-coil structure with a molecular weight of about 300,000. Collagen existing in skin, cartilage, bone and tendon is composed of two α1 chains and one α2 chain of roughly one thousand amino acids each. The α1 sequence is completely known and substantial sequences of the α2 chain have been elucidated.

Collagenase effects an ultra-specific cleavage of collagen at a site one quarter the length of the molecule from the C-terminus in each of the three chains.

Collagenase is produced by rheumatoid synovial cells at a rate higher than it is produced by normal cells and the destructive events of rheumatoid arthritis can be correlated with the generation of collagenase. Collagenase has also been found to be involved in disease states resulting in tissue destruction of the stomach, eye, middle ear, peridontal membranes and skin. The administration of a collagenase inhibitor to prevent tissue destruction is an indicated method of treatment for disease states involving proteolytic destruction of collagen.

Collagenase is a metallo enzyme of molecular weight about 40,000 with a requirement of zinc. The enzyme is known to be inhibited by chelating agents such as ethylenediaminetetraacetic acid, o-phenanthroline, penicillamine and disulfide reducing agents such as cysteine and dithiothreitol as well as a number of poorly characterized naturally occurring substances.

DESCRIPTION OF THE INVENTION

In accordance with this invention there is provided a group of polypeptides which inhibit the activity of the enzyme collagenase. The polypeptides of this invention present the structural formula:

$$X-R_1-R_2-[R_3]_n-NH_2$$

in which

X is hydrogen, alkanoyl of 2 to 6 carbon atoms, cycloalkylcarbonyl of 6 to 8 carbon atoms or alkoxycarbonyl of 2 to 6 carbon atoms;

$R_1$ is Cys-, 3-mercapto-Val-, p-Glu-Cys-, p-Glu-3-mercapto-Val- or Pro-Gln-Gly-;

$R_2$ is Leu-, Ile- or Val-;

$R_3$ is Ala-, Ala-Gly- or Ala-Gly-Arg-; and n is 0 or 1;

or a pharmaceutically acceptable salt thereof.

The pharmaceutically acceptable salts of the polypeptides of this invention include salts derived from either organic or inorganic acids such as acetic, lactic, succinic, benzoic, salicylic, methanesulfonic, toluenesulfonic, hydrochloric, sulfuric or phosphoric acid, and the like. Desired salts may be produced from other salts via conventional treatment with ion exchange resins. The N-terminal acyl groups depicted as X in the structural formula, supra, are preferably alkanoyl or cycloalkanoyl moieties as defined and more preferably either the acetyl or cyclopentylcarbonyl groups.

The compounds of this invention are produced by conventional solution phase techniques or solid phase techniques employing a benzhydrylamine polystyrene resin support. Thus, the individual amino acids or preformed di- or tri-peptides necessary for the formation of the desired polypeptide or their activated derivatives are condensed with formation of carbamide (—CONH—) bondings in the desired order of succession while temporarily protecting any reactive group which could undesirably enter into the condensation reaction. In the case of cysteine and penicillamine, the side chain mercapto protecting group may be acetamidomethyl, trityl, carbamoyl, thioethyl, thiotertiarybutyl or preferably p-methoxybenzyl. For arginine, the protecting groups may be nitro, benzyloxycarbonyl, adamantyloxycarbonyl, tert-butyloxycarbonyl or preferably the tosyl group. The applicable α-amino protecting groups are those well known to the art or preferably tert-butyloxycarbonyl.

The inhibitory effect of the compounds of this invention toward collagenase was determined following the procedure of Sellers et al., Biochem. J. 167, 353-360 (1977) whereby the 2 mM of the inhibitor being tested is incubated at 35° C. for from 5 to 18 hours (depending upon the potency of the collagenase) with collagen and collagenase (buffered with Tris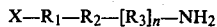—CaCl2; pH 7.4). The collagen is acetyl $^{14}C$ collagen. The samples are centrifuged and an aliquot removed for assay on a scintillation counter. Because native collagen forms insoluble fibrils under the test conditions, the supernatant liquid contains radioactivity as a measure of hydrolysis. The collagenase activity in the presence of 2 mM inhibitor is compared to activity in a control devoid of inhibitor and the results reported as percent inhibition of collagenase activity. Each of the compounds of this invention have been established as active collagenase inhibitors by the test procedure.

Thus, the compounds of this invention are useful in the treatment of disease states involving excessive collagen destruction by collagenase such as rheumatoid arthritis and diseases evidenced by tissue destruction of the stomach, eye, middle ear, peridontal membranes, skin. The dosage of the collagenase inhibitors of this invention will vary with the mode of administration (oral, parenteral, topical, intramuscular, etc.) and the condition of the specific patient under treatment. Proper dosing may be readily established by initial administration of small amounts of the inhibitor, ca. 100 μg/kg. followed by increased doses until the optimum effect is achieved in a specific human or non-human mammalian patient. When sustained release treatment is desired, the polypeptides may be placed in conventional depot dosage forms such as a Silastic capsule or slow release pellet formulations conventional to the art.

The following examples illustrate the preparation of typical representative compounds of the invention. After each preparative example, the percent inhibition of collagenase activity at the 2 mM level of inhibition in accordance with the previously described standart testing procedure is provided.

EXAMPLE 1

H-L-Cys-L-Ile-NH2

2.05 g (6 meq) of t-Boc-s-p-methoxybenzyl-L-cysteine and 973 mg (6 meq) of carbonyl diimidazole were reacted 2.5 hr. at ambient temperature in 10 ml of tetrahydrofuran. L-Isoleucine amide.HCl (1.1 g) in DMF containing 0.86 ml of triethylamine was added to the above at 0° C. and reacted over 72 hours allowing icebath to melt. The reaction mixture was evaporated under reduced pressure (<30° C.) and the residue dissolved in ethyl acetate (EtOCa)/H2O and filtered. The phases were separated and the EtOAc layer was extracted with 5% KHSO₄, saturated KHCO₃ and dried over Na₂SO₄. The drying agent was removed was removed by filtration and the EtOAc removed under reduced pressure (<30° C.) and the residue dried in vacuo over KOH. 2½ gm TLC (S. G. CHCl₃/MeOH 25/1 I₂ indicator) indicated the presence of a major $R_f$ 0.67 and minor component in the protectd dipeptide amide and it was purified on a silica gel column using CHCl₃/MeOH 25/1. Fractions 41-64 were combined on the basis of TLC S. G. CHCl₃/MeOH 25:1 and I₂ detection $R_f$ 0.65 and evaporated to dryness in vacuo <30° C. Wt. 1.1 gm.

The protected dipeptide was deprotectd with HF in the presence of 10 ml of anisole for 1 hr. at 0° C. The HF was removed in vacuo and the residue triturated 3 times with Et₂O and dried in a stream of N₂. The residue was triturated with 0.2 N HOAc filtered and the filtrate lyophylized, 533 mg of crude H-Cys-Ile-NH₂.

150 mg of the crude peptide were chromatographed on Sephadex G-10 using 0.2 N HOAc as elutant. One ml fractions were collected at a flow rate of 15 ml per hour and fractions 33-36 were combined based on TLC S.G., BAW, ninhydrin and lyophylized 79 mg. $R_f$ (BAW). Amino acid ratio: Cys 0.94, Ile 1.0, NH₃ 0.8. Percent inhibition collagenase: 35.

EXAMPLE 2

L-pGlu-L-Cys-L-Ile-NH₂

5 Grams benzhydrylamine hydrochloride resin (Beckman) were treated in a solid phase peptide synthesizer with 30% triethylamine in MeCl₂ for five minutes and washed successively, with MeCl₂ (1×) and DMF (2×) and coupled with 6 gm t-Boc-L-isoleucine, 4 gm HOBT and 4 ml DIC overnight. After successive washings with DMF (1×), MeCl₂ (2×) MeOH (1×) and MeCl₂ (2×) the amino acyl resin was ninhydrin slightly positive and was recoupled with the above reagents in the same amount. After the usual washing at this stage it was still ninhydrin slightly positive and after washing the resin with DMF—30% triethylamine followed by DMF it was recoupled with 12 gm t-Boc-L-isoleucine, 8 gm HOBT and 8 ml DIC over 4 days. It was washed as usual at this step previously and coupled with 8.5 gm t-Boc-S-p-methoxybenzyl-L-cysteine, 4 gm HOBT and 4 ml DIC overnight. After the previously described washing at this stage, the peptidyl resin was slightly ninhydrin positive and was recoupled with 8.5 gm t-Boc-S-p-methoxybenzyl-L-cysteine, 4 gm HOBT and 4 ml DIC overnight. After the usual washing at this stage the peptidyl resin was deprotected with TFA, washed in the previously described manner for this stage, and coupled with 6 gm pyro-L-glutamic acid, 4 gm HOBT and 4 ml DIC as previously described for this step. After the usual washing at this stage it was recoupld two succeeding times with the same amounts of reagents as previously described. The peptidyl resin was slightly ninhydrin positive, was washed with diethyl ether, and dried in vacuo.

The peptidyl resin was deprotected and cleaved with HF in the presence of 7 ml of anisole for 1 hour at 0° C. The HF was removed in vacuo overnight the residue washed 3 times with diethyl ether, dried in a current of nitrogen and triturated with 150 ml of 0.2 N HOAc for five minutes and filtered. The filtrate was lyophylized. 346 mg of crude pGlu-Cys-Ile-NH₂.

63 mg of the above were purified by chromatography on Sephadex G-10 using 0.2 HOAc as solvent at a flow rate of 15 ml per hour with collection of 1 ml fractions.

Collected fractions 67-76 were combined on the basis of TLC SG.BAW system and peptide chlorine spray and lyophylized ($R_f$ 0.47 in BAW system), 27 mg. Amino acid analysis of the product gave the following ratios: Glu, 1.0, Cys (not recovered), Ile 0.90, NH₃ 1.2. Percent inhibition collagenase: 75.

EXAMPLE 3

CH₃CO-Pro-Gln-Gly-Ile-Ala-Gly-NH₂

8 Grams of benzhydrylamine hydrochloride resin (Bachem) were treated twice in a solid phase peptide synthesizer with 30% triethylamine in methylene chloride (MeCl₂) for five minutes and washed successively, with methylene chloride and dimethylformamide (DMF) and coupled with 5 gm t-Boc-Glycine, 4 gm hydroxybenzotriazole (HOBT) and 4 ml diisopropylcarbodiimide (DIC) overnight in DMF. After successive washings with DMF (1×), MeCl₂ (2×), MeOH and MeCl₂ the resin gave a slightly positive ninhydrin reaction and was recoupled with 5 gm t-Boc Glycine, 4 gm HOBT and 4 ml DIC as previously. After successive washings with DMF (once) MeCl₂ (twice), MeOH and MeCl₂, the t- Boc-glycyl resin was trace ninhydrin positive and was deprotected for 30 minutes with 50% trifluoroacetic acid in MeCl₂ followed by washing with MeCl₂ (once) 30% triethylamine in DMF (twice) and DMF (twice). The glycyl-resin was coupled with 5.5 gm t-Boc-L-alanine, 4 grams HOBT and 4 ml DIC overnight. The peptidyl resin was washed successively with DMF, MeCl₂, MEOH and MeCl₂ as previously, was ninhydrin slightly positive and was recoupled with 5.5 gm t-Boc-L-alanine 4 gm HOBT and 4 ml DIC as previously.

It was trace ninhydrin positive at this point, was deprotected with 50% TFA in MeCl₂ as previously washed with MeCl₂, DMF-triethylamine, and DMF as previously and coupled with 6 gm t-Boc-L-isoleucine, 4 gm HOBT and 4 ml DIC as described for the previous coupling. The peptidyl resin after the usual washing at this step was ninhydrin trace positive was deprotected with TFA washed as previously described for this step and coupled with 6 gm t-Boc-glycine, 4 gm HOBT and 4 ml DIC as previously described. The peptidyl-resin was recoupled twice one with 6 gm t-Boc-glycine and once with 10 gm t-Boc-glycine being trace ninhydrin positive was washed as previously for this step; deprotected with TFA as previously described washed as previously described for this step and coupled with 7.4 gm t-Boc-L-glutamine, 4 gm HOBT and 4 ml DIC as described for the previous couplings. The peptidyl resin was slightly ninhydrin positive and was recoupled with 7.4 gm t-Boc glycine as previously, washed as usual for this step and coupled with 6.5 gm t-Boc-L-proline, 4 gm HOBT and 4 ml DIC as previous. Being slightly ninhydrin positive it was recoupled with 6.5 gm t-Boc-L-proline as described previously and was deprotected with TFA as usual at this stage, washed as usual and coupled with 10 gm acetyl imidazole in DMF overnight. The peptidyl-resin was ninhydrin negative after the second washing at this stage was washed once with Et₂O and dried in vacuo over KOH.

The above peptidyl resin was deprotected and cleaved with HF in the presence of 8 ml of anisole for 1 hour at 0° C. The HF removed in vacuo and the residue washed 3 times with diethyl ether, dried in a current of nitrogen and triturated with 150 ml of 0.2 N HOAc for five minutes and filtered. The filtrate was lyophilized giving 976 mg crude AcPro-Gln-Gly-Ile-Ala-Gly-NH$_2$.

94 mg of crude peptide were partitioned on Sephadex G-25 (medium) using the system BuOH, acetic acid, water 4:1:5 at a flow rate of 25 ml per hour and collecting 1 ml fractions. Collected fractions 74–82 were combined on the basis of TLC silica gel (Merck), BAW system using peptide-chlorine spray for detection (R$_f$ 0.39) evaporated to dryness in vacuo below 30° C. and lyophylized from 0.2 N HOAc gave 13 mg of title compound. Amino acid analysis of the product gave the following ratios: Pro 1.03, Glu 1.1, Ala 1.0, Gly 2.3, Ile 1.07, NH$_3$ 2.2. Percent inhibition collagenase: 35.

What is claimed is:

1. A compound of the formula:

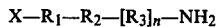

in which

X is hydrogen, alkanoyl of 2 to 6 carbon atoms, cycloalkylcarbonyl of 6 to 8 carbon atoms or alkoxycarbonyl of 2 to 6 carbon atoms;

R$_1$ is Cys-, 3-mercapto-Val-, p-Glu-Cys-, p-Glu-3-mercapto-Val- or Pro-Gln-Gly-;

R$_2$ is Leu-, Ile- or Val-;

R$_3$ is Ala-, Ala-Gly- or Ala-Gly-Arg-; and n is 0 or 1;

or a pharmaceutically acceptable salt thereof.

2. The compound of claim 1 which is L-Cys-L-Ile-NH$_2$ or a pharmaceutically acceptable salt thereof.

3. The compound of claim 1 which is L-p-Glu-L-Cys-L-Ile-NH$_2$ or a pharmaceutically acceptable salt thereof.

4. The compound of claim 1 which is L-Pro-L-Gln-Gly-L-Ile-L-Ala-Gly-NH$_2$ or a pharmaceutically acceptable salt thereof.